(12) United States Patent
Francischelli

(10) Patent No.: US 7,294,143 B2
(45) Date of Patent: Nov. 13, 2007

(54) DEVICE AND METHOD FOR ABLATION OF CARDIAC TISSUE

(75) Inventor: David E. Francischelli, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 8 days.

(21) Appl. No.: 10/356,868

(22) Filed: Feb. 3, 2003

(65) Prior Publication Data

US 2004/0015219 A1 Jan. 22, 2004

Related U.S. Application Data

(60) Provisional application No. 60/381,217, filed on May 16, 2002.

(51) Int. Cl.
*A61F 7/00* (2006.01)
*A61B 18/18* (2006.01)
(52) U.S. Cl. ......................... 607/105; 606/41
(58) Field of Classification Search ............... 606/41, 606/45–50; 607/101–105; 604/21, 22; 128/898
See application file for complete search history.

(56) References Cited

U.S. PATENT DOCUMENTS

| | | | |
|---|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |

(Continued)

OTHER PUBLICATIONS

J. Thorac Cardiovascular Surg 1991; 101:402-5—The Surgical Treatment of atrial fibrillation (Summary of the current concepts of the mechanisms of atrial flutter and atrial fibrillation) by James L. Cox, MD; Richard B. Schuessler, PHD; and John P. Boineau, MD.

(Continued)

*Primary Examiner*—Michael Peffley
(74) *Attorney, Agent, or Firm*—Mike Jaro; Jeffrey J. Hohenshell

(57) ABSTRACT

Methods for delivering precise amounts of fluid into cardiac tissue for the purpose of facilitating ablation of the tissue along a desired lesion line. One method injects fluid through a hollow needle. The injected fluid can be a highly conductive fluid injected in conjunction with radiofrequency ablation to create an ablative virtual electrode. The injected conductive fluid can provide deeper and narrower conduction paths and resulting lesions. Radiofrequency ablation can be performed at the same time as the fluid injection, using the injection device as an electrode, or subsequent to the fluid injection, using a separate device. In some methods, the injected fluid is a protective fluid, injected to protect tissue adjacent to the desired lesion line. Fluid delivery can be endocardial, epicardial, and epicardial on a beating heart. The present methods find one use in performing maze procedures to treat atrial fibrillation.

57 Claims, 4 Drawing Sheets

U.S. PATENT DOCUMENTS

| | | | |
|---|---|---|---|
| 4,022,215 A | 5/1977 | Benson | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |
| 4,204,438 A | 5/1980 | Binaris et al. | 81/9.22 |
| 4,207,897 A | 6/1980 | Lloyd et al. | |
| 4,248,224 A | 2/1981 | Jones | |
| 4,275,734 A | 6/1981 | Mitchiner | |
| 4,278,090 A | 7/1981 | van Gerven | |
| 4,377,168 A | 3/1983 | Rzasa et al. | |
| 4,519,389 A | 5/1985 | Gudkin et al. | |
| 4,598,698 A | 7/1986 | Siegmund | |
| 4,601,290 A | 7/1986 | Effron et al. | |
| 4,664,110 A | 5/1987 | Schanzlin | |
| 4,719,825 A | 1/1988 | LaHaye et al. | 81/9.22 |
| 4,736,749 A | 4/1988 | Lundback | |
| 4,779,611 A | 10/1988 | Grooters et al. | |
| 4,802,475 A | 2/1989 | Weshahy | |
| 4,815,470 A | 3/1989 | Curtis et al. | |
| 4,872,346 A | 10/1989 | Kelly-Fry et al. | |
| 4,916,922 A | 4/1990 | Mullens | |
| 4,917,095 A | 4/1990 | Fry et al. | |
| 4,936,281 A | 6/1990 | Stasz | |
| 4,946,460 A | 8/1990 | Merry et al. | |
| 5,013,312 A | 5/1991 | Parins et al. | |
| 5,029,574 A | 7/1991 | Shimamura et al. | |
| 5,044,165 A | 9/1991 | Linner et al. | |
| 5,078,713 A | 1/1992 | Varney | |
| 5,080,102 A | 1/1992 | Dory | |
| 5,080,660 A | 1/1992 | Buelina | |
| 5,100,388 A | 3/1992 | Behl et al. | |
| 5,108,390 A | 4/1992 | Potocky et al. | |
| 5,147,355 A | 9/1992 | Freidman et al. | |
| 5,178,133 A | 1/1993 | Pena | |
| 5,207,674 A | 5/1993 | Hamilton | |
| 5,217,860 A | 6/1993 | Fahy et al. | |
| 5,222,501 A | 6/1993 | Ideker et al. | |
| 5,224,943 A | 7/1993 | Goddard | |
| 5,228,923 A | 7/1993 | Hed | |
| 5,231,995 A | 8/1993 | Desai | |
| 5,232,516 A | 8/1993 | Hed | |
| 5,254,116 A | 10/1993 | Baust et al. | |
| 5,263,493 A | 11/1993 | Avitall | |
| 5,269,291 A | 12/1993 | Carter | |
| 5,275,595 A | 1/1994 | Dobak, III | |
| 5,277,201 A | 1/1994 | Stern | |
| 5,281,213 A | 1/1994 | Milder et al. | |
| 5,281,215 A | 1/1994 | Milder | |
| 5,295,484 A | 3/1994 | Marcus et al. | |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowler | |
| 5,334,181 A | 8/1994 | Rubinsky et al. | |
| 5,334,193 A | 8/1994 | Nardella | |
| 5,348,554 A | 9/1994 | Imran et al. | |
| 5,353,783 A | 10/1994 | Nakao et al. | |
| 5,354,258 A | 10/1994 | Dory | |
| 5,361,752 A | 11/1994 | Moll et al. | |
| 5,385,148 A | 1/1995 | Lesh et al. | |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,403,309 A | 4/1995 | Coleman et al. | |
| 5,403,311 A * | 4/1995 | Abele et al. | 606/49 |
| 5,405,376 A | 4/1995 | Mulier et al. | |
| 5,409,483 A | 4/1995 | Campbell et al. | |
| 5,423,807 A | 6/1995 | Milder | |
| 5,423,811 A | 6/1995 | Imran et al. | |
| 5,427,119 A | 6/1995 | Swartz et al. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,443,463 A | 8/1995 | Stern et al. | |
| 5,443,470 A | 8/1995 | Stern et al. | |
| 5,450,843 A | 9/1995 | Moll et al. | |
| 5,452,582 A | 9/1995 | Longsworth | |
| 5,452,733 A | 9/1995 | Sterman et al. | |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,560,362 A | 10/1996 | Silwa, Jr. et al. | |
| 5,562,720 A | 10/1996 | Stern et al. | |
| 5,569,241 A | 10/1996 | Edwards | |
| 5,571,088 A | 11/1996 | Lennox et al. | |
| 5,571,215 A | 11/1996 | Sterman et al. | |
| 5,573,532 A | 11/1996 | Chang et al. | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,588,432 A | 12/1996 | Crowley | |
| 5,590,657 A | 1/1997 | Cain et al. | |
| 5,595,183 A | 1/1997 | Swanson et al. | |
| 5,607,462 A | 3/1997 | Imran | |
| 5,617,854 A | 4/1997 | Munsif | |
| 5,630,837 A | 5/1997 | Crowley | |
| 5,637,090 A | 6/1997 | McGee et al. | |
| 5,643,197 A | 7/1997 | Brucker et al. | |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,697,536 A | 12/1997 | Eggers et al. | |
| 5,697,882 A | 12/1997 | Eggers et al. | |
| 5,697,925 A | 12/1997 | Taylor | |

| | | | | | | |
|---|---|---|---|---|---|---|
| 5,697,927 A | 12/1997 | Imran et al. | | 6,142,993 A | 11/2000 | Whayne et al. |
| 5,697,928 A | 12/1997 | Walcott et al. | | 6,142,994 A | 11/2000 | Swanson et al. |
| 5,713,942 A | 2/1998 | Stern | | 6,152,920 A | 11/2000 | Thompson et al. |
| 5,716,389 A | 2/1998 | Walinsky et al. | | 6,161,543 A | 12/2000 | Cox et al. |
| 5,718,241 A | 2/1998 | Ben-Haim et al. | | 6,165,174 A | 12/2000 | Jacobs et al. |
| 5,718,701 A | 2/1998 | Shai et al. | | 6,217,528 B1 | 4/2001 | Koblish et al. |
| 5,720,775 A | 2/1998 | Lanard | | 6,217,576 B1 | 4/2001 | Tu et al. |
| 5,722,402 A | 3/1998 | Swanson et al. | | 6,224,592 B1 | 5/2001 | Eggers et al. |
| 5,730,074 A | 3/1998 | Peter | | 6,231,518 B1 | 5/2001 | Grabek et al. |
| 5,730,127 A | 3/1998 | Avitall | | 6,235,024 B1 | 5/2001 | Tu |
| 5,730,704 A | 3/1998 | Avitall | | 6,237,605 B1 | 5/2001 | Vaska et al. |
| 5,735,280 A | 4/1998 | Sherman et al. | | 6,238,347 B1 | 5/2001 | Nix et al. |
| 5,755,760 A | 5/1998 | Maguire et al. | | 6,238,393 B1 | 5/2001 | Mulier |
| 5,769,846 A | 6/1998 | Edwards et al. | | 6,245,061 B1 | 6/2001 | Panescu et al. |
| 5,782,828 A | 7/1998 | Chen et al. | | 6,245,064 B1 | 6/2001 | Lesh et al. |
| 5,785,706 A | 7/1998 | Bednarek | | 6,245,065 B1 | 6/2001 | Panescu et al. |
| 5,788,636 A | 8/1998 | Curley | | 6,251,092 B1 | 6/2001 | Qin et al. |
| 5,792,140 A | 8/1998 | Tu et al. | | 6,251,128 B1 | 6/2001 | Knopp et al. |
| 5,797,960 A | 8/1998 | Stevens et al. | | 6,270,471 B1 | 8/2001 | Hechel et al. |
| 5,800,428 A | 9/1998 | Nelson et al. | | 6,293,943 B1 | 9/2001 | Panescu et al. |
| 5,800,482 A | 9/1998 | Pomeranz et al. | | 6,296,619 B1 | 10/2001 | Brisken et al. |
| 5,810,802 A | 9/1998 | Panescu et al. | | 6,302,880 B1 | 10/2001 | Schaer |
| 5,827,216 A | 10/1998 | Igo et al. | | 6,311,692 B1 | 11/2001 | Vaska et al. |
| 5,836,947 A | 11/1998 | Fleischman et al. | | 6,312,383 B1 | 11/2001 | Lizzi et al. |
| 5,840,030 A | 11/1998 | Ferek-Petric et al. | | 6,314,962 B1 | 11/2001 | Vaska et al. |
| 5,844,349 A | 12/1998 | Oakley et al. | | 6,314,963 B1 | 11/2001 | Vaska et al. |
| 5,846,187 A | 12/1998 | Wells et al. | | 6,325,797 B1 | 12/2001 | Stewart et al. |
| 5,846,191 A | 12/1998 | Wells et al. | | 6,328,736 B1 | 12/2001 | Mulier |
| 5,849,028 A | 12/1998 | Chen | | 6,332,881 B1 | 12/2001 | Carner et al. |
| 5,871,523 A | 2/1999 | Fleischman et al. | | 6,358,248 B1 | 3/2002 | Mulier |
| 5,871,525 A | 2/1999 | Edwards et al. | | 6,361,531 B1 | 3/2002 | Hissong |
| 5,873,845 A | 2/1999 | Cline et al. | | 6,364,876 B1 | 4/2002 | Erb et al. |
| 5,876,399 A | 3/1999 | Chia et al. | | 6,368,275 B1 | 4/2002 | Sliwa et al. |
| 5,879,295 A | 3/1999 | Li et al. | | 6,371,955 B1 | 4/2002 | Fuimaono et al. |
| 5,879,296 A | 3/1999 | Ockuly et al. | | 6,383,151 B1 | 5/2002 | Diederich et al. |
| 5,881,732 A | 3/1999 | Sung et al. | | 6,385,472 B1 | 5/2002 | Hall et al. |
| 5,882,346 A | 3/1999 | Pomeranz et al. | | 6,398,792 B1 | 6/2002 | O'Connor |
| 5,885,278 A | 3/1999 | Fleischman | | 6,409,722 B1 | 6/2002 | Hoey |
| 5,893,848 A | 4/1999 | Negus et al. | | 6,413,254 B1 | 7/2002 | Hissong et al. |
| 5,895,417 A | 4/1999 | Pomeranz et al. | | 6,419,648 B1 | 7/2002 | Vitek et al. |
| 5,897,553 A | 4/1999 | Mulier et al. | | 6,425,867 B1 | 7/2002 | Vaezy et al. |
| 5,897,554 A | 4/1999 | Chia et al. | | 6,430,426 B2 | 8/2002 | Avitall |
| 5,899,898 A | 5/1999 | Arless et al. | | 6,440,130 B1 | 8/2002 | Mulier |
| 5,899,899 A | 5/1999 | Arless et al. | | 6,443,952 B1 | 9/2002 | Mulier |
| 5,902,289 A | 5/1999 | Swartz et al. | | 6,447,507 B1 | 9/2002 | Bednarek et al. |
| 5,904,711 A | 5/1999 | Flom et al. | | 6,461,314 B1 | 10/2002 | Pant et al. |
| 5,906,580 A | 5/1999 | Kline-Schoder et al. | | 6,461,956 B1 | 10/2002 | Patterson |
| 5,906,587 A | 5/1999 | Zimmon | | 6,464,700 B1 | 10/2002 | Koblish et al. |
| 5,906,606 A | 5/1999 | Chee et al. | | 6,471,697 B1 | 10/2002 | Lesh |
| 5,908,029 A | 6/1999 | Knudson et al. | | 6,471,698 B1 | 10/2002 | Edwards et al. |
| 5,916,214 A | 6/1999 | Cosio et al. | | 6,474,340 B1 | 11/2002 | Vaska et al. |
| 5,921,924 A | 7/1999 | Avitall | | 6,475,216 B2 | 11/2002 | Mulier |
| 5,921,982 A | 7/1999 | Lesh et al. | | 6,484,727 B1 | 11/2002 | Vaska et al. |
| 5,927,284 A | 7/1999 | Borst et al. | | 6,488,680 B1 | 12/2002 | Francischelli |
| 5,928,191 A | 7/1999 | Houser et al. | | 6,494,902 B2 * | 12/2002 | Hoey et al. ................. 607/105 |
| 5,931,810 A | 8/1999 | Grabek | | 6,502,575 B1 | 1/2003 | Jacobs et al. |
| 5,931,848 A | 8/1999 | Saadat | | 6,514,250 B1 | 2/2003 | Jahns |
| 5,954,661 A | 9/1999 | Greenspan et al. | | 6,527,767 B2 | 3/2003 | Wang et al. |
| 5,971,980 A | 10/1999 | Sherman | | 6,537,248 B2 | 3/2003 | Mulier |
| 5,971,983 A | 10/1999 | Lesh | | 6,537,272 B2 | 3/2003 | Hoey |
| 5,993,447 A | 11/1999 | Blewett et al. | | 6,558,382 B2 | 5/2003 | Jahns |
| 6,007,499 A | 12/1999 | Martin et al. | | 6,584,360 B2 | 6/2003 | Francischelli |
| 6,012,457 A | 1/2000 | Lesh | | 6,585,732 B2 | 7/2003 | Mulier |
| 6,016,811 A | 1/2000 | Knopp et al. | | 6,605,084 B2 | 8/2003 | Acker et al. |
| 6,042,556 A | 3/2000 | Beach et al. | | 6,610,055 B1 | 8/2003 | Swanson et al. |
| 6,063,081 A | 5/2000 | Mulier et al. | | 6,610,060 B2 | 8/2003 | Mulier |
| 6,064,914 A * | 5/2000 | Trachtenberg ............... 607/102 | | 6,613,048 B2 | 9/2003 | Mulier |
| 6,071,279 A | 6/2000 | Whayne et al. | | 6,645,199 B1 | 11/2003 | Jenkins et al. |
| 6,088,894 A | 7/2000 | Oakley | | 6,656,175 B2 | 12/2003 | Francischelli |
| 6,096,037 A | 8/2000 | Mulier | | 6,692,450 B1 | 2/2004 | Coleman |
| 6,113,592 A | 9/2000 | Taylor | | 6,699,240 B2 | 3/2004 | Francischelli |
| 6,117,101 A | 9/2000 | Diederich et al. | | 6,702,811 B2 | 3/2004 | Stewart et al. |
| 6,120,496 A | 9/2000 | Whayne et al. | | 6,706,038 B2 | 3/2004 | Francischelli |

| | | |
|---|---|---|
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier et al. |
| 6,807,968 B2 | 10/2004 | Francischelli |
| 6,827,715 B2 | 12/2004 | Francischelli |
| 6,849,073 B2 | 2/2005 | Hoey |
| 6,852,091 B2 * | 2/2005 | Edwards et al. ............ 604/22 |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

OTHER PUBLICATIONS

J. Thorac Cardiovasc Surg 1991; 101: 584-92—The surgical treatment of atrial fibrillation (Surgical Technique) by James L. Cox, MD.

Ann Thorac Surg 1996; 62: 1796-800 / Simple Left Atrial Procedure for Chronic Artrial Fibrillation Associated With Mitral Valve Disease by Taijiro Sueda, MD; Hideyuki Nagata, MD; Hiroo Shikata, MD; Kazumasa Orihashi, MD; Satoru Morita, MD; Masafumi Sueshiro, MD; Kenji Okada, MD and Yuichiro Matsuura, MD.

PACE vol. 15 (Supplement Sep.) 1992 pp. 1368-1373 / Transcoronary Chemical Ablation of Arrhythmias by Paul Nellens; Sinan Gursoy; Erik Andries and Pedro Brugada.

European Heart Journal, vol. 12, 1991, pp. 1234-1237 / Chemical ablation by subendocardial injection of ethanol via catheter—preliminary results in the pig heart by P. Weismuller; U. Mayer; P. Richter; F Heieck; M. Kochs and V. Hombach.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91:2235-2244, 1995.

Cox et al., "Modification of the Maze Procedure for Atrial Flutter and Atrial Fibrillation. I. Rational and Surgical Results," The Journal of Thoracic Cardiovascular Surgery 110:473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Suppl 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12): 1132-1144.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Chitwood, "Will C. Sealy, MD: The Father of Arrhythmia Surgery—The Story of the Fisherman with a Fast Pulse," Annals of Thoracic Surgery 58:1228-1239, 1994.

Gallagher et al., "Cryosurgical Ablation of Accessory Atrioventrical Connections: A Method for Correction of the Pre-excitation Syndrome," Circulation 55(3):471-479, 1977.

Sealy, "Direct Surgical Treatment of Arrhythmias: The Last Frontier in Surgical Cardiology," Chest 75(5):536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5):495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984, 1990.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594, 1994.

* cited by examiner

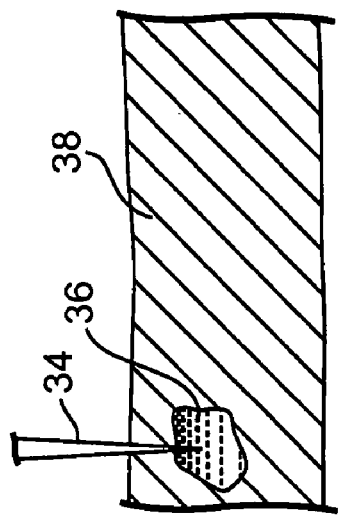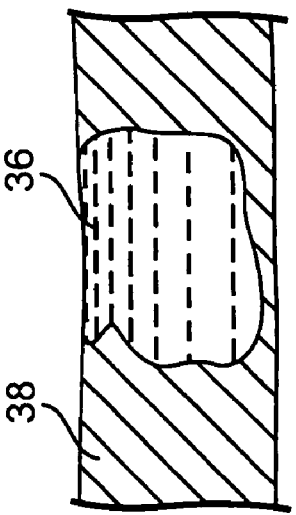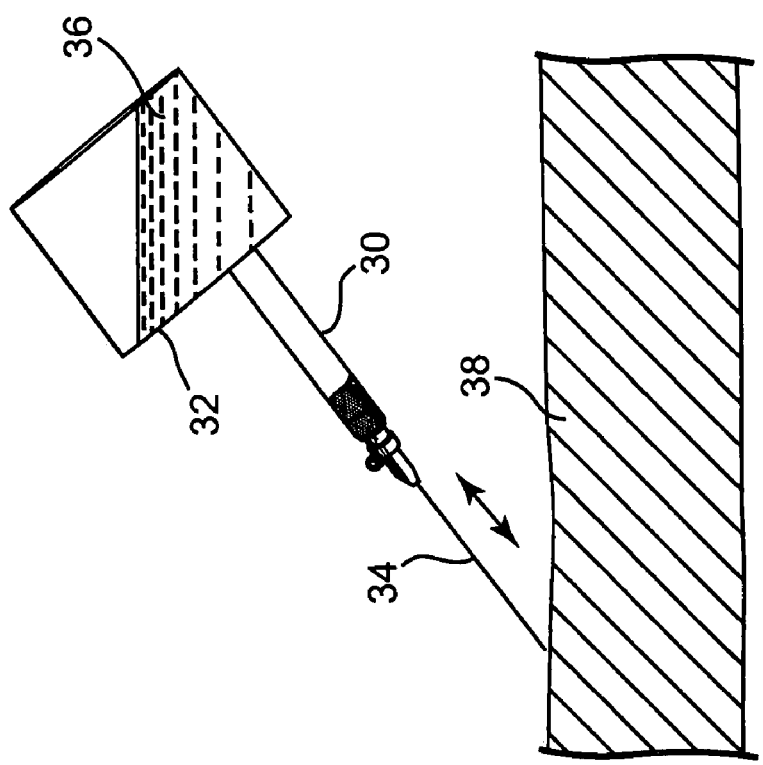

DEVICE AND METHOD FOR ABLATION OF CARDIAC TISSUE

RELATED APPLICATIONS

The present application claims priority to U.S. provisional patent application Ser. No. 60/381,217, filed on May 16, 2002, titled DEVICE AND METHOD FOR ABLATION OF CARDIAC TISSUE, herein incorporated by reference in its entirety. The present invention is related commonly assigned U.S. patent application Ser. No. 10/356,909, filed on Feb. 3, 2003, titled DEVICE AND METHOD FOR NEEDLE-LESS INTERSTITIAL INJECTION OF FLUID FOR ABLATION OF CARDIAC TISSUE.

FIELD OF THE INVENTION

The present invention relates generally to the field of devices for cardiac surgery, and more specifically to devices for ablation of cardiac tissue.

BACKGROUND OF THE INVENTION

The present invention is directed toward treatment of tachyarrhythmias, which are heart rhythms in which a chamber or chambers of the heart exhibits an excessively fast rhythm. In particular, the present invention is directed toward treatment of tachycardias, which are due to the presence of ectopic foci within the cardiac tissue or due to the presence of aberrant condition pathways within the cardiac tissue.

There are many medical treatments that involve instances of cutting, ablating, coagulating, destroying, or otherwise changing the physiological properties of tissue. These techniques can be used beneficially to change the electrophysiological properties of tissue. For example, by ablation of cardiac tissue to cure various cardiac conditions. Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract. This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles.

The aberrant conductive pathways create abnormal, irregular, and sometimes life-threatening heart rhythms, called arrhythmias. An arrhythmia can take place in the atria, for example, as in atrial tachycardia, atrial fibrillation or atrial flutter. The arrhythmia can also take place in the ventricle, for example, as in ventricular tachycardia.

The lesions used to treat atrial fibrillation, are typically long and thin and are carefully placed to interrupt the conduction routes of the most common reentry circuits. More specifically, the long thin lesions are used to create a maze pattern that creates a convoluted path for electrical propagation within the left and right atria. The lesions direct the electrical impulse from the SA node along a specified route through all regions of both atria, causing uniform contraction required for normal atrial transport function. The lesions finally direct the impulse to the AV node to activate the ventricles, restoring normal atrioventricular synchrony. Several surgical approaches have been developed with the intention of treating atrial fibrillation. One particular example is known as the "maze procedure," as is disclosed by Cox, J L et al. in "The surgical treatment of atrial fibrillation. I. Summary" Thoracic and Cardiovascular Surgery 101(3), pp. 402-405 (1991); and also by Cox, J L in "The surgical treatment of atrial fibrillation. IV. Surgical Technique", Thoracic and Cardiovascular Surgery 101(4), pp. 584-592 (1991), both of which are incorporated by reference herein in their entireties. In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996), which is incorporated herein by reference in its entirety.

When modifying the electrophysiological properties of cardiac tissue by ablation, or by other means of destroying tissue to create lesions, physicians must carefully place the lesions. Otherwise, tissue will be unnecessarily destroyed. In addition, the heart is in close proximity to nerves and other nervous tissue and the destruction of this tissue will result in severe harm to the patient. Anatomical methods are used to locate the areas to be ablated or otherwise modified. In other words, the physician locates key structures such as the mitral valve annulus and the pulmonary veins. Lesions are typically formed that block propagations near these structures. Additional lesions are then formed which connect these lesions and complete the so-called "maze pattern." However, the exact lesion pattern, and number of lesions created, can vary from patient to patient.

The surgical "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

Although successful at treating AF, the surgical maze procedure is quite complex and is currently performed by only a few skilled cardiac surgeons in conjunction with other open heart procedures. Tools that could reliably duplicate the Maze incisions by other means (e.g. radiofrequency, laser, microwave, ultrasound energy) will reduce the time and invasiveness required for the maze procedure and make it more accessible to more surgeons. Problems faced by these methods, however, include (a) the creation of continuous, linear lesions in the atria for the prevention of atrial fibrillation, (b) minimization of clotting and thromboembolism, (c) the effect of heat loss due to circulating blood, (d) minimization of lesion width and minimization of atrial debulking, (e) conforming to an irregular myocardial thickness, (f) adaptability to a variety of lesion geometries and (g) usefulness from either the endocardial surface of an open heart, or the epicardial surface of a beating heart.

Injection of alcohol into heart tissue has also been employed to ablate cardiac tissue. Alcohol may be delivered to blood vessels supplying the tissue to be ablated, as described in "Transcoronary Chemical Ablation of Arrhythmias", by Nellens et al, Pace Vol. 15, pages 1368-1373, September 1992. Alternatively, alcohol can be delivered directly to the tissue to be ablated by means of a needle inserted through a catheter, as described in "Chemical Ablation by Subendocardial Injection of Ethanol via Catheter—Preliminary Results in the Pig Heart", by Weismuller et al, European Heart Journal, Volume 12, pages 1234-1239, 1991.

SUMMARY OF THE INVENTION

This invention relates to a device and method for ablation of cardiac tissue in which a hand-held instrument having a hollow needle is used to deliver precise amounts of liquids into cardiac tissue for purposes of ablation of the tissue along a desired lesion line.

In one aspect of the invention, a reciprocating needle device like that disclosed in U.S. Pat. No. 4,204,438, which is incorporated by reference in its entirety, is used to repeatedly penetrate cardiac tissue and deliver a cytotoxic agent to the cardiac tissue. The cytotoxic agent is used to "draw" a lesion on the myocardium by the repeated introduction of the needle and injection of cytotoxic fluid while moving the tip of the device along the desired lesion pattern. Because of the motor-driven reciprocating action of the device, the lesion pattern can be completed rapidly by the surgeon. A manually operated switch on the housing of the device is capable of energizing and de-energizing the device as desired by the operator and an eccentric drive advances and retracts the needle from the housing. The depth of needle penetration can be adjusted to control the depth at which the cytotoxic fluid is delivered to the tissue but preferably the depth of needle penetration enables the cytotoxic fluid to be injected into the tissue so that it extends through the entire thickness of the tissue. The hollow needle is filled with the cytotoxic agent. The cytotoxic fluid can be loaded into the needle a little at a time or it can be filled by means of a fluid reservoir. The delivery of the fluid can occur passively as the needle is inserted into the tissue or it can be actively injected into the tissue according to needle position. The fluid delivery can be performed endocardially, epicardially, and epicardially on a beating heart.

In yet another aspect of the invention, a non-reciprocating metering needle assembly like that disclosed in U.S. Pat. No. 4,719,825, which is incorporated by reference in its entirety, is use to repeatedly penetrate cardiac tissue and deliver a cytotoxic agent to the cardiac tissue. After the hollow needle has been inserted into the myocardial tissue, the device is activated by the operator to deliver a predetermined, metered amount of the cytotoxic agent into the myocardium. The needle is then withdrawn from the cardiac tissue and advanced to a second location along the desired lesion pattern where it is inserted into the myocardium and another predetermined metered amount of cytotoxic agent is dispensed into the myocardial tissue. In this manner, the device is advanced stepwise along the desired lesion line by the operator in order to complete the lesion.

In yet another aspect of the invention, a device as described above is utilized in combination with radiofrequency ablation. The needle can be connected to one pole of a radiofrequency generator while the other pole of the generator is connected to a large indifferent electrode. Rather than a cytotoxic agent, the needle delivers a conductive liquid such as a saline solution that creates an ablative virtual electrode when delivered into the tissue through the needle. The device is advanced along a desired lesion line on the tissue as the needle is advanced into and retracted from the tissue. Delivery of the conductive liquid and the ablative radiofrequency energy is synchronized to form the virtual electrode and ablate the tissue along the desired lesion line.

In yet another aspect of the invention, a device as described above is utilized in combination with a conventional radiofrequency ablation device such as the Cardioblate® pen sold by Medtronic, Inc. Rather than a cytotoxic agent, the needle delivers a conductive liquid such as a hypertonic saline solution to the tissue. The device is advanced along a desired lesion line on the tissue as the needle is advanced into and retracted from the tissue. Delivery of the conductive liquid is made into the tissue along the desired lesion line. The conductive tip of the Cardioblate pen is then drawn along the desired lesion line while applying radiofrequency energy to the tissue. The hypertonic saline solution that creates a low impedance electrical pathway to ground such that the resultant lesion is deeper and narrower than would normally result from the use of the conventional radiofrequency ablation device.

In yet another aspect of the invention, a device as described above is utilized in order to deliver a protective fluid in order to protect certain areas of cardiac tissue, such as tissue near vessels and valves. For example, a hypotonic fluid can be used as a protective fluid in order to increase the electrical impedance of the tissue to be protected relative to the surrounding tissues, essentially insulating the protected tissue from the electrical current of the radiofrequency ablation device. This aspect of the invention can be combined with one or more of the other aspects of the invention in which a conductive liquid is delivered to a first portion of cardiac tissue along a desired lesion line and a protective fluid is delivered to a second portion of cardiac tissue spaced apart from the desired lesion line. This can be readily accomplished by a device having a plurality of spaced-apart needles with centrally located needles delivering the conductive liquid and other needles on one or both sides of the centrally located needles which deliver the protective fluid. As the radiofrequency ablation device, such as the Cardioblate pen, is advanced along the desired lesion line a narrower and deeper lesion would result with this technique.

In yet another aspect of the invention, a device as described above is utilized in order to deliver an ink or dye to the cardiac tissue in order to identify the position of the lesion line on the cardiac tissue and to identify portions of tissue along the lesion line where the lesion has been completed. For example, the ink or dye can be added to the cytotoxic fluid in order to identify portions of tissue which have received the cytotoxic fluid and that those portions create a complete lesion along the desired lesion line. Alternatively, the ink or dye can be added to the conductive liquid in order to identify the portions of tissue which has been ablated by the radiofrequency energy of a virtual electrode. Again the completeness of the lesion line is indicated by the presence of the ink or dye. Alternatively, the ink or dye can be added to the conductive liquid in order to identify the position of the desired lesion line so that the Cardioblate pen or other radiofrequency ablation device can be guided along the line that has been established by the delivery of the conductive fluid. In yet another aspect, the ink or dye can be thermochromic such that it changes color when heated to a temperature which indicates that a lesion has been formed by the application of radiofrequency energy. Typically, temperatures above about 50 to 55 degrees C. are required to cause cell death in an ablative lesion made by radiofrequency ablation and the photochromic material would preferably change color in that temperature range.

BRIEF DESCRIPTION OF THE DRAWINGS

FIG. 3 is a schematic view of a device with a reciprocating needle operating according to the invention.

FIG. 4 is a side sectional view of a needle delivering a fluid into tissue according to the invention.

FIG. 5 is a side sectional view of fluid delivered according to the invention that has diffused into tissue near its point of delivery.

DETAILED DESCRIPTION OF THE INVENTION

The following detailed description should be read with reference to the drawings, in which like elements in different drawings are numbered identically. The drawings, which are not necessarily to scale, depict selected embodiments and are not intended to limit the scope of the invention. Several forms of the invention have been shown and described, and other forms will now be apparent to those skilled in art. It will be understood that embodiments shown in drawings and described below are merely for illustrative purposes, and are not intended to limit the scope of the invention as defined in the claims which follow.

Figure 2:
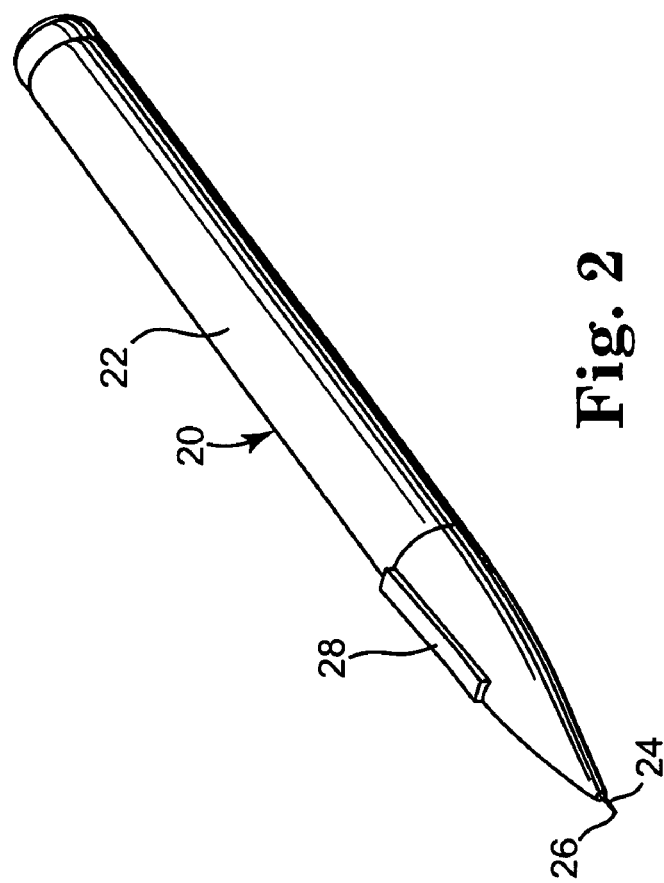
FIG. 2 is a perspective view of a prior art device suitable for use in the present invention.
Figure 1:
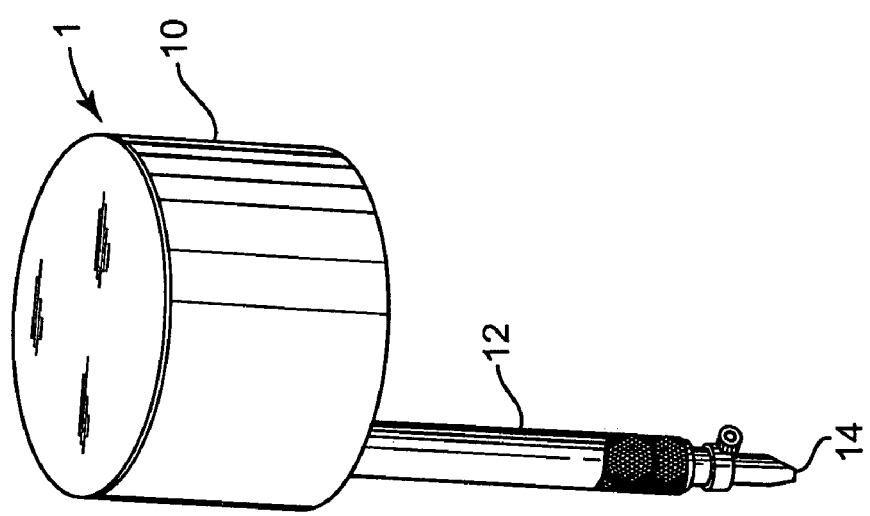
FIG. 1 is a perspective view of a prior art device suitable for use in the present invention

This invention relates to a device and method for ablation of cardiac tissue in which a hand-held instrument having a hollow needle is used to deliver precise amounts of liquids into cardiac tissue for purposes of ablation of the tissue along a desired lesion line. FIGS. 1 and 2 show prior art devices suitable for the practice of the present invention. FIG. 1 shows a reciprocating needle device 1 as disclosed in U.S. Pat. No. 4,204,438. The reciprocating needle device 1 includes a motor housing 10 and a needle housing 12. The needle housing 12 has an opening 14 through which a needle reciprocates. The device 1 may be held by hand by a surgeon and used to repeatedly penetrate cardiac tissue by a reciprocating action of the needle and deliver a cytotoxic agent to the cardiac tissue. FIG. 2 shows a non-reciprocating metering needle device 20 like that disclosed in U.S. Pat. No. 4,719,825. The metering needle device 20 has a barrel portion 22 that can be held by hand, a tip portion 24 through which a needle 26 extends and a switch 28. A surgeon can advance the needle 26 into myocardial tissue and then deliver a metered amount of a cytotoxic agent from the needle 26 by activating the switch 28 on the metering needle device 20. Some tattoo pens are also believed suitable for practicing the present invention. The tattoo pens preferably provide a longer than conventional needle travel path and also provide a stronger than conventional driving force for driving the needle or needles through the longer path.

The cytotoxic agent is an agent which has cytotoxic properties and can be delivered as an injectable liquid or a liquid suspension. Preferably the cytotoxic substance has potent cytotoxic properties that destroys cell function without affecting protein structure and scaffolding. Also preferably, the cytotoxic agent has limited and controllable diffusion properties through extracellular spaces. Also preferably the cytotoxic agent has a fleeting effect such that the compound washes out of the systemic circulation quickly. Alkylating agents such as cytotaxan or melphalan or their active metabolites are preferred.

Figure 11:
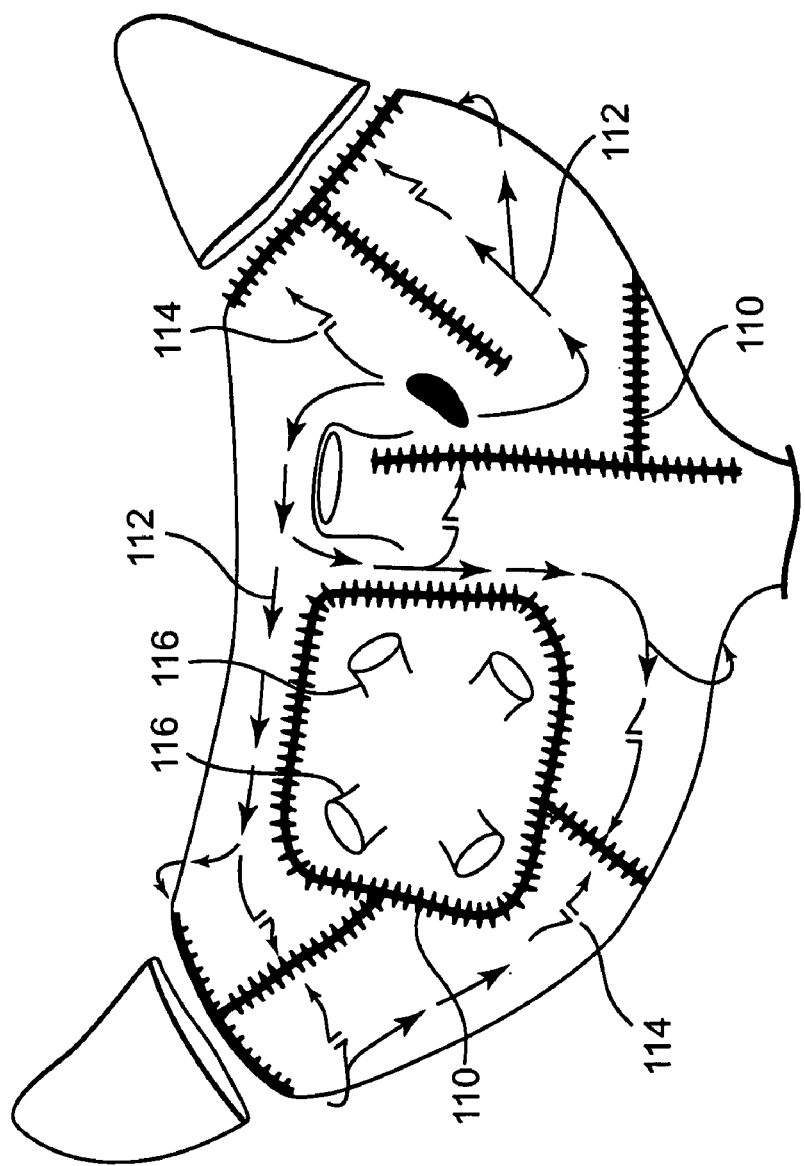
FIG. 11 is a schematic view of the heart showing various maze lesions that can be formed according to the invention.

The cytotoxic agent is used to "draw" a lesion on the myocardium by the repeated introduction of the needle and injection of cytotoxic fluid while moving the tip of the device along the desired lesion pattern. FIG. 11 shows some possible generally linear lesion patterns 110 that are capable of interrupting conductive pathways 112 and 114.

Referring now to FIGS. 3-5, a reciprocating needle device 30 can have a reservoir 32 and a hollow, reciprocating needle 34 through which the fluid 36 can be delivered into myocardial tissue 38. The needle 34 may be tapered to allow for easy penetration of the tissue 38 and delivery of fluid 36 into the tissue 38. Following delivery of the fluid, the needle is withdrawn and the fluid 36 diffuses into the tissue 38. Needles 34a-34c also represent varying depth needles included within an array or linear array of needles. The needle array can be advanced along the desired lesion path and the needles inserted together, insuring multiple fluid delivery depths along the path. Such a phased linear array of needles also can reduce the force required to enter the myocardium, relative to a constant dept array, as the time of entry into the tougher outer layer occurs at different times.

Figure 8:
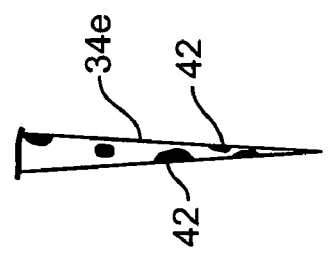
FIG. 8 is a side view of a distal portion of a needle showing multiple fluid openings for delivery of fluid according to the present invention.
Figure 6:
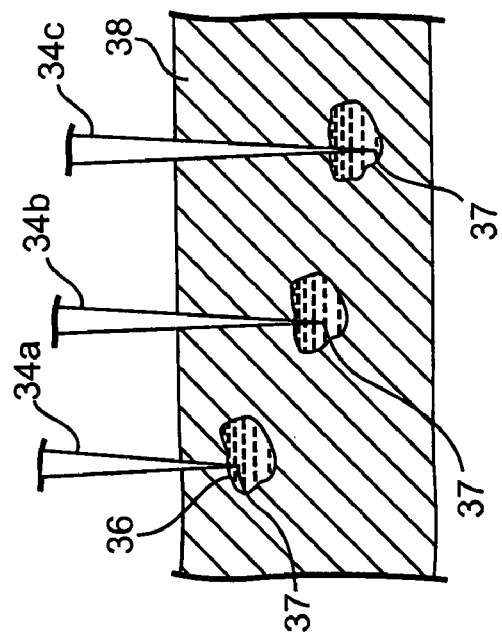
FIG. 6 is a side sectional view showing needles delivering fluid according to the invention into tissue at varying depths.
Figure 7:
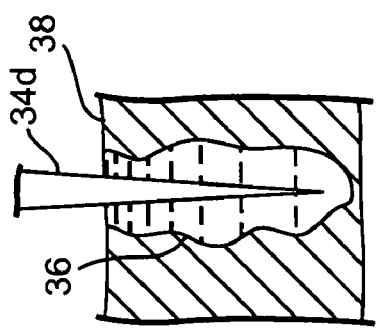
FIG. 7 is a side sectional view of a needle delivering fluid according to the invention during reciprocation of the needle.

Referring now to FIGS. 6-8, the depth of penetration for needles 34a-c can be adjusted to control the depth at which the cytotoxic fluid 36 is delivered to the tissue 38 through injection ports or orifices 37. The needle 34d can also be adjusted to deliver the cytotoxic fluid as the needle 34d is inserted and/or withdrawn in order to provide delivery of fluid 36 at various depths. Also, the needle may be provided with injection ports or openings 42 which will deliver fluid from a plurality of side openings or ports along the length of the needle 34e. The delivery of the fluid can therefore occur passively as the needle is inserted into the tissue or it can be actively injected into the tissue according to needle position.

Figure 9:
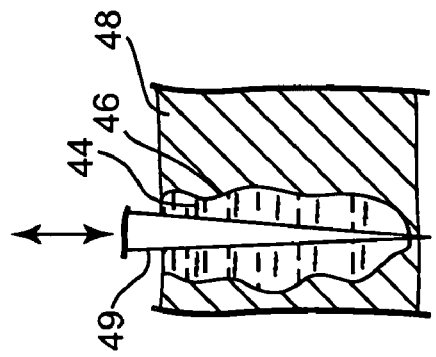
FIG. 9 is a side sectional view of a lesion created by the application of radiofrequency energy according to the invention.

Referring now to FIG. 9, the device can also be utilized in combination with radiofrequency ablation. An ablative lesion 44 can be created in tissue 48 by a needle connected to a radiofrequency generator (not shown) as a conductive fluid 46 is delivered through the needle 49 into the tissue 48. Rather than a cytotoxic agent, the needle delivers a conductive liquid such as a saline solution that creates an ablative virtual electrode when delivered into the tissue through the needle. The device is advanced along a desired lesion line on the tissue as the needle is advanced into and retracted from the tissue. Delivery of the conductive liquid and the ablative radiofrequency energy can be synchronized to form the virtual electrode and ablate the tissue along the desired lesion line.

Figure 10:
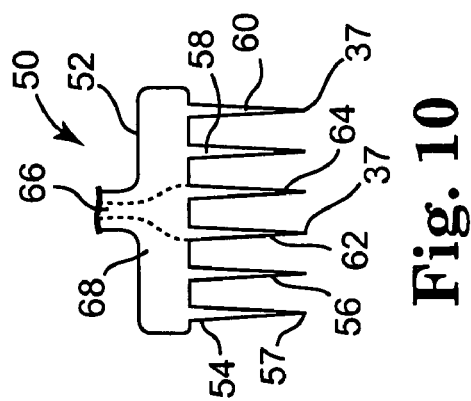
FIG. 10 is a fragmentary, schematic, side sectional view of a linear array of needles which can be used for delivering protective fluid about a delivered cytotoxic and/or conductive fluid.

FIG. 10 illustrates a linear array of needles 50 including an injection manifold 52. Linear array 50 includes outer needles 54, 56, 58, and 60, and inner needles 62 and 64. Inner needles 62 and 64 are fed by a first fluid delivery lumen 66 while outer needles 54-60 are fed by a second fluid delivery lumen 68. The inner needles can deliver a conductive and/or cytotoxic fluid, while the outer needles can deliver a protective fluid, described below.

Referring now to FIG. 11, some possible generally linear lesion patterns 110 are shown that are capable of interrupting conductive pathways 112 and 114. The lesion patterns can be made as described above or in combination with a conventional radiofrequency ablation device such as the Cardioblate pen sold by Medtronic, Inc. (not shown). Rather than a cytotoxic agent, the needle delivers a conductive liquid such as a hypertonic saline solution to the tissue. The device is advanced along a desired lesion line 110 on the tissue as the needle is advanced into and retracted from the tissue. Delivery of the conductive liquid is made into the tissue along the desired lesion line 110. The conductive tip of the Cardioblate pen is then drawn along the desired lesion line 110 while applying radiofrequency energy to the tissue. The hypertonic saline solution that creates a low impedance electrical pathway to ground such that the resultant lesion is deeper and narrower than would normally result from the use of the conventional radiofrequency ablation device.

A protective fluid can also be used when making the linear lesions 110 in order to protect certain areas of cardiac tissue, such as tissue near vessels and valves like the pulmonary veins 116. For example, a hypotonic fluid can be used as a protective fluid in order to increase the electrical impedance of the tissue to be protected relative to the surrounding tissues, essentially insulating the protected tissue from the electrical current of the radiofrequency ablation device. Alternatively, the protective fluid can be a thermally protective fluid such as a chilled fluid which protects tissue adjacent to the intended lesion from being overheated. This aspect of the invention can be combined with one or more of the other aspects of the invention in which a conductive liquid is delivered to a first portion of cardiac tissue along a desired lesion line and a protective fluid is delivered to a second portion of cardiac tissue spaced apart from the desired lesion line. This can be readily accomplished by a device having a plurality of spaced-apart needles with centrally located needles delivering the conductive liquid and other needles on one or both sides of the centrally located needles which deliver the protective fluid, as discussed with respect to FIG. 10. As the radiofrequency ablation device, such as the Cardioblate pen, is advanced along the desired lesion line a narrower and deeper lesion would result with this technique.

Also, the device as described above can be utilized in order to deliver an ink or dye to the cardiac tissue in order to identify the position of the lesion line 110 on the cardiac tissue and to identify portions of tissue along the lesion line 110 where the lesion has been completed. For example, the ink or dye can be added to the cytotoxic fluid in order to identify portions of tissue which have received the cytotoxic fluid and that those portions create a complete lesion along the desired lesion line. Alternatively, the ink or dye can be added to the conductive liquid in order to identify the portions of tissue which has been ablated by the radiofrequency energy of a virtual electrode. Again the completeness of the lesion line is indicated by the presence of the ink or dye. Alternatively, the ink or dye can be added to the conductive liquid in order to identify the position of the desired lesion line so that the Cardioblate pen or other radiofrequency ablation device can be guided along the line that has been established by the delivery of the conductive fluid. Dyes such as those used for tattoos are believed suitable, as are some tissue dyes. Toluene blue and methylene blue are examples of dyes believed suitable for use in the present invention.

In yet another aspect, the ink or dye can be thermochromic such that it changes color when heated to a temperature which indicates that a lesion has been formed by the application of radiofrequency energy. Typically, temperatures above about 50 to 55 degrees C. are required to cause cell death in an ablative lesion made by radiofrequency ablation and the photochromic material would preferably change color in that temperature range.

In still another aspect, the injected fluid can include a viscous enhancing agent or fluid added to reduce or retard fluid diffusion after delivery. Reducing the diffusion of a cytotoxic and/or conductive fluid can reduce the width of the resulting lesion. Reducing the diffusion of a protective fluid can maintain the protective fluid in a desired position adjacent the cytotoxic and/or conductive fluid, to serve its protective function. Viscous fluids such as dextrose or glycerol may be added to increase the viscosity of a delivered fluid. The viscous fluids or agents can provide a fluid viscosity of at least about twice that of water.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

The invention claimed is:

1. A method for ablation of myocardial tissue comprising:
providing a hand-held instrument having a first hollow needle coupled to a first fluid delivery lumen for delivery of a first fluid and a second hollow needle coupled to a second fluid delivery lumen for delivery of a second fluid;
selecting a desired line of ablation on a surface of the tissue;
applying the first needle to the tissue at a first portion of the desired line of ablation such that it penetrates the tissue;
applying the second needle to the tissue at a second portion spaced apart from the desired line of ablation such that it penetrates the tissue;
delivering a predetermined amount of the first fluid into the penetrated tissue to facilitate ablation of the first portion of tissue along the desired lesion line; and
delivering a predetermined amount of the second fluid into the penetrated tissue to protect the second portion of tissue spaced apart from the desired lesion line.

2. A method according to claim 1 wherein the first needle reciprocates to repeatedly penetrate and deliver the first fluid to the myocardial tissue along the desired line of ablation.

3. A method according to claim 2 wherein the first fluid is introduced into the first needle by means of a first fluid reservoir and the second fluid is introduced into the second needle by means of a second fluid reservoir.

4. A method according to claim 1 wherein the first fluid applied to the myocardial tissue is a cytotoxic agent applied in amount effective to ablate the myocardial tissue.

5. A method according to claim 4 wherein the cytotoxic agent draws a lesion on the myocardium by the repeated introduction of the first needle and injection of cytotoxic fluid while moving the device along the desired lesion pattern.

6. A method according to claim 1 wherein delivery of the first or second fluid is actively injected into the tissue according to the first or second needle position in the myocardial tissue.

7. A method according to claim 1 wherein the first or second fluid is delivered to the myocardium in a predetermined, metered amount.

8. A method according to claim 1 wherein the first needle is withdrawn from the myocardial tissue and advanced to a second location along the desired line of ablation where the first needle is inserted into the myocardium and another amount of the first fluid is dispensed into the myocardial tissue.

9. A method according to claim 1 also comprising the step of applying radiofrequency ablation through the needle.

10. A method according to claim 9 wherein the needle delivers a conductive liquid.

11. A method according to claim 10 wherein the conductive liquid is a saline solution that creates an ablative virtual electrode when delivered in combination with the application of radiofrequency ablation.

12. A method according to claim 9 wherein the needle is moved along the desired lesion line on the tissue as the needle is advanced into and retracted from the tissue.

13. A method according to claim 12 wherein the liquid and the ablative radiofrequency energy are synchronized to form a virtual electrode and ablate the tissue along the desired lesion line.

14. A method according to claim 1 also comprising completing delivery of fluid along the desired lesion line and subsequently applying to the desired lesion line radiofrequency ablation.

15. A method according to claim 14 wherein the fluid is a hypertonic saline solution.

16. A method according to claim 1 wherein the fluid is a protective fluid which increases the electrical impedance of the myocardial tissue.

17. A method according to claim 16 wherein the protective fluid is delivered to tissue near a heart valve.

18. A method according to claim 16 wherein the protective fluid is delivered to tissue near a blood vessel.

19. A method according to claim 16 wherein the fluid is a hypotonic fluid.

20. A method according to claim 1 wherein the fluid comprises an ink or dye.

21. A method according to claim 1 wherein the fluid comprises a cytotoxic fluid.

22. A method according to claim 1 wherein the fluid comprises a conductive fluid.

23. A method according to claim 1 wherein the fluid comprises a hypotonic fluid.

24. A method according to claim 20 also comprising visually inspecting the ink or dye on the lesion line.

25. A method according to claim 20 wherein the ink or dye changes color at a predetermined temperature.

26. A method according to claim 1, wherein the fluid comprises a viscosity enhancing agent.

27. A method according to claim 1, wherein the delivering is performed epicardially.

28. A method according to claim 1, wherein the delivering is performed endocardially.

29. A method according to claim 1, wherein the provided hand-held instrument further comprises a needle array comprising a plurality of hollow needles in addition to the hollow needle, where in the applying includes applying the plurality of needles to penetrate the tissue, wherein the delivering includes delivering fluid into the penetrated tissue through the plurality of needles.

30. A method according to claim 1 wherein the second fluid comprises a thermally protective fluid.

31. A method for ablation of myocardial tissue comprising:
provproviding a hand-held instrument having a first injection port for injecting a first fluid into myocardial tissue and a second injection port for injecting a second fluid into myocardial tissue;
selecting a desired line of ablation on a surface of the tissue;
applying the first injection port to the tissue at a portion of the desired line of ablation;
applying the second injection port to the tissue at a second portion spaced apart from the desired line of ablation;
delivering a predetermined amount of the first fluid into the myocardial tissue to facilitate ablation of the tissue along the desired lesion line; and
delivering a predetermined amount of the second fluid into the myocardial tissue to protect tissue spaced apart from the desired lesion line.

32. A method according to claim 31 wherein the fluid applied to the myocardial tissue includes a cytotoxic agent applied in amount effective to ablate the myocardial tissue.

33. A method according to claim 31 wherein the first or second fluid is delivered to the myocardium in a predetermined, metered amount.

34. A method according to claim 31 wherein the injection device is advanced to a second location along the desired line of ablation and another amount of first fluid is dispensed into the myocardial tissue.

35. A method according to claim 31 also comprising the step of applying radiofrequency ablation through the injection device.

36. A method according to claim 35 wherein the injection device delivers a conductive liquid.

37. A method according to claim 36 wherein the conductive liquid is a saline solution that creates an ablative virtual electrode when delivered in combination with the application of radiofrequency ablation.

38. A method according to claim 35 wherein the injection port is moved along the desired lesion line on the tissue as the fluid is injected into the tissue.

39. A method according to claim 38 wherein the liquid and the ablative radiofrequency energy are synchronized to form a virtual electrode and ablate the tissue along the desired lesion line.

40. A method according to claim 31 also comprising completing delivery of fluid along the desired lesion line and subsequently applying to the desired lesion line radiofrequency ablation.

41. A method according to claim 40 wherein the fluid is a hypertonic saline solution.

42. A method according to claim 31 wherein the fluid is a protective fluid which increases the electrical impedance of the myocardial tissue.

43. A method according to claim 42 wherein the protective fluid is delivered to tissue near a heart valve.

44. A method according to claim 42 wherein the protective fluid is delivered to tissue near a blood vessel.

45. A method according to claim 42 wherein the fluid is a hypotonic fluid.

46. A method according to claim 31 wherein the fluid comprises an ink or dye.

47. A method according to claim 31 wherein the fluid comprises a cytotoxic fluid.

48. A method according to claim 46 wherein the fluid comprises a conductive fluid.

49. A method according to claim 46 wherein the fluid comprises a protective fluid.

50. A method according to claim 46 also comprising visually inspecting the ink or dye on the lesion line.

51. A method according to claim 31 wherein the ink or dye changes color at a predetermined temperature.

52. A method according to claim 31, wherein the fluid comprises a viscosity enhancing agent.

53. A method according to claim 31, wherein the delivering is performed epicardially.

54. A method according to claim 31, wherein the delivering is performed epicardially on a beating heart.

55. A method according to claim 31, wherein the delivering is performed endocardially.

56. A method according to claim 31 wherein the second fluid comprises a thermally protective fluid.

57. A method according to claim 31 wherein the second fluid comprises a hypotonic protective fluid.

* * * * *